(12) United States Patent
Mulvaney et al.

(10) Patent No.: US 6,548,168 B1
(45) Date of Patent: Apr. 15, 2003

(54) STABILIZED PARTICLES AND METHODS OF PREPARATION AND USE THEREOF

(75) Inventors: Paul Charles Mulvaney, Coburg (AU); Luis Manuel Liz-Marzan, Vigo (ES)

(73) Assignee: The University of Melbourne, Parkville (AU)

( * ) Notice: Subject to any disclaimer, the term of this patent is extended or adjusted under 35 U.S.C. 154(b) by 0 days.

(21) Appl. No.: 09/530,161

(22) PCT Filed: Oct. 28, 1998

(86) PCT No.: PCT/AU98/00896

§ 371 (c)(1),
(2), (4) Date: Aug. 8, 2000

(87) PCT Pub. No.: WO99/21934

PCT Pub. Date: May 6, 1999

(30) Foreign Application Priority Data

Oct. 28, 1997 (AU) .............................................. PP0044

(51) Int. Cl.[7] .............................................. B32B 5/16
(52) U.S. Cl. ................ 428/402; 428/403; 428/404; 428/405; 428/407; 427/2.12; 427/2.24; 427/229; 427/299; 427/301; 427/384; 427/399; 427/404; 427/414
(58) Field of Search ................ 428/402, 403, 428/404, 405, 407; 427/2.02, 2.24, 301, 229, 414, 404, 299, 399, 384

(56) References Cited

U.S. PATENT DOCUMENTS

| | | | |
|---|---|---|---|
| 4,994,429 A | 2/1991 | Wieserman et al. | 502/401 |
| 5,034,297 A | 7/1991 | Yoerger | 430/108.3 |
| 5,609,907 A | * 3/1997 | Natan | 427/2.12 |

FOREIGN PATENT DOCUMENTS

| | | | |
|---|---|---|---|
| EP | 721976 | | 7/1996 |
| GB | 2316068 | | 2/1998 |
| WO | WO 90/15666 | * | 12/1990 |
| WO | 90/15666 | | 12/1990 |
| WO | WO 91/09678 | * | 7/1991 |
| WO | 91/09678 | | 7/1991 |
| WO | WO 93/26019 | * | 12/1992 |
| WO | WO 93/15117 | * | 8/1993 |
| WO | 93/15117 | | 8/1993 |
| WO | 93/26019 | | 12/1993 |

OTHER PUBLICATIONS

Derwent Abstract Accession No.: 97–039417/04, JP 08–297295 A, (UBE Nitto Kasei Co) Nov. 12, 1996.
Derwent Abstract Accession No.: 28559B/15, (Dainippon Tokyo KK) Mar. 3, 1929.
Derwent Abstract Accession No.: 91–343599/47. (Nippon Sheet Glass KK) Oct. 11, 1991.

* cited by examiner

*Primary Examiner*—Leszek Kiliman
(74) *Attorney, Agent, or Firm*—Christensen O'Connor Johnson Kindness PLLC

(57) ABSTRACT

A method of stabilizing particles with an insulating, semi-conducting and/or metallic coating and stabilized particles prepared thereby are disclosed. In addition, particles stabilized by an insulating, semiconducting and/or metallic coating, wherein said coating is attached to said particles via a bifunctional ligand are provided, as is a method is provided for determining the presence of an analyte in a sample comprising incubating the sample with a ligand bound to a coated particle, capable of specifically binding to the analyte and capable of providing a detectable signal and detecting the presence of a ligand-coated particle:analyte complex as indicating the presence of the analyte in the sample.

53 Claims, 7 Drawing Sheets

STABILIZED PARTICLES AND METHODS OF PREPARATION AND USE THEREOF

This is a United States national stage application of International application No. PCT/AU98/00896, filed Oct. 28, 1998, the benefit of the filing date of which is hereby claimed under 35 U.S.C. §120, which in turn claims the benefit of Australian application No. PP 0044, filed Oct. 28, 1997, the benefit of the filing date of which is hereby claimed under 35 U.S.C. §119.

TECHNICAL FIELD

The present invention relates generally to stabilized particles and methods for their production. More specifically, the present invention relates to particles having a size of less than about 0.1 microns or 100 nm, such as nanoparticles, that are stabilized by an insulating, semiconducting and/or metallic coating.

BACKGROUND OF THE INVENTION

Nanosized metal particles have a wide variety of potential uses, ranging from nonlinear optical switching and high-density information storage to immunolabeling and tracer diffusion studies in concentrated dispersions. Nanoparticles have unique optical, electrical and magnetic properties. Nanoparticles are typically optically transparent. A major difficulty with large-scale implementation is that metal colloids have complicated double-layer structures, and their stability is controlled by both electronic equilibria and ionic/polymer adsorption.

Semiconductor materials also have an extraordinary importance in technology mainly because of their special electronic properties that arise from a separation between the conduction and valence bands. When semiconductor materials are prepared in the nanoparticle-size range, the density of electronic states changes in a systematic manner which strongly influences the optical and electronic properties of the material. The surface of semiconductor nanoparticles is highly defective from the point of view of semiconductor physics, so that energy levels within the energy gap of the bulk solid occur due to reconstruction of atomic positions.

The preparation of at least nanosized particles can be facilitated greatly by careful choice of the ligands or stabilizers used to prevent particle coalescence. For example, polymeric stabilizers are very efficacious dispersants in aqueous solution, whereas long chain surfactants or chemically specific ligands are more widely used in organic media. Alternatively, stabilization can be achieved through compartmentalization of the particles in micelles or microemulsions, while immobilisation in glasses or sol gels is the preferred technique when redox reactions of the particles with the matrix need to be avoided. More recently, Langmuir-Blodgett (LB) films have been used as particle stabilizers, and electrodeposition of surfactant-stabilized metal particles has been used to create ordered two-dimensional crystals. These various techniques not only permit the synthesis of pure metal particles, but also allow the preparation of semiconductor particles and nanosized alloys, mixed metal particles, and coated particles as well as particles with nonspherical geometries (e.g., rods or platelets).

However, many of the stabilizers employed affect the solid state properties of the particles. To circumvent this problem it is desirable to find a stabilizer that prevents particle coalescence. In addition, it is preferable that the stabilizer be chemically inert and optically transparent. These conditions can be met by, for example, silica, a coating material used in a wide range of industrial colloid products ranging from paints and magnetic fluids to high quality paper coatings.

The use of silica as a stabilizer rather than an organic molecule has several advantages. In addition to preventing coagulation of the particles during chemical or electronic processes, the silica shells are expected to act as a passivant due to a disordered (amorphous) structure that can be accommodated to that of the underlying particles.

However, some particles, for example, gold metal, have very little affinity for silica because they do not form a passivating oxide film in solution. furthermore, there are usually adsorbed carboxylic acids or other organic anions present on the surface of such metals to stabilize the particles against coagulation. These stabilizers also render the metal surface vitreophobic.

A need exists for a method of coating particles with a suitable agent such as silica to impart stability to the particles and to the surface thereof without substantially affecting their properties, in particular their optical properties such as fluorescence.

SUMMARY OF THE INVENTION

Accordingly, it is an object of the invention to address the above-identified need in the art.

According to one aspect of the present invention there is provided a method of stabilizing particles with an insulating, semiconducting and/or metallic coating. The method comprises: (i) admixing a source of particles with a source of coating to provide a particle-coating admixture; (ii) adding to the particle-coating admixture a bifunctional ligand represented by structural formula (I)

wherein A is a first functional group that attaches to the particle, or to a coating formed on the particle, selected from the group consisting of thiols, amines, phosphines, phosphates, borates, tetra alkyl ammoniums, carboxyls, silicates, siloxys, selenates, arsenates and aluminates, B is a functional group that activates the surface of the core particle for nucleation of a coating layer and is selected from the group consisting of thiols, amines, phosphines, carboxyls, silicates, siloxys, silanes, selenates, arsenates and aluminates, and X is an optional linking group.

In an alternate embodiment, the source of particles is first admixed with the bifunctional ligand to provide a particle-ligand admixture; (ii) adding to particle-ligand admixture a source of coating; and (iii) allowing the bifunctional ligand and coating to deposit on the particles.

According to another aspect of the invention, stabilized particles are provided wherein the particles are prepared by either of the aforementioned methods.

According to yet another aspect of the present invention, there are provided particles stabilized by an insulating, semiconducting and/or metallic coating, wherein said coating is attached to said particles via a bifunctional ligand.

According to still another aspect of the present invention, a method is provided for determining the presence of an analyte in a sample suspected of containing the analyte comprising incubating the sample with a ligand that specifically binds to the analyte and is capable of providing a detectable signal, wherein the ligand comprises a coated particle as disclosed herein.

According to a further aspect of the present invention there is provided a pigment or paint colourant which is composed wholly or partly of the stabilized particle defined above.

These and other embodiments of the subject invention will readily occur to those of ordinary skill in the art in view of the disclosure herein.

DETAILED DESCRIPTION OF THE INVENTION

Figure 1:
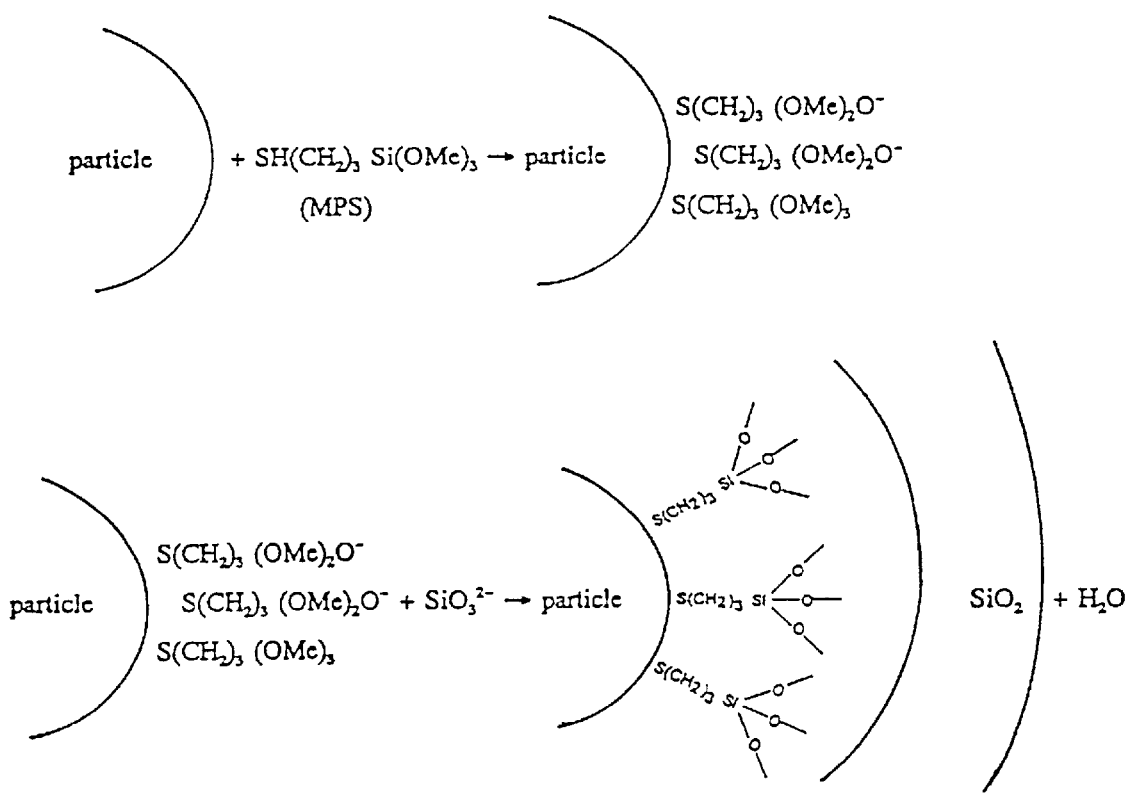
FIG. 1 is an illustration of the surface reactions involved in providing a silica coating on a core particle using the bifunctional ligand 3-mercaptopropyl trimethoxysilane.

The practice of the methods of the present invention will employ, unless otherwise indicated, conventional techniques of synthetic organic chemistry that are within the skill of the art. Such techniques are explained fully in the literature. See, e.g., Kirk-Othmer's Encyclopedia of Chemical Technology; House's Modern Synthetic Reactions and C. S. Marvel and G. S. Hiers' text, *ORGANIC SYNTHESIS*, Collective Volume 1.

As used in this specification and the appended claims, the singular forms "a," "an" and "the" include plural references unless the content clearly dictates otherwise. Thus, for example, reference to a "functional group" includes more than one such group, reference to "a coating layer" includes more than one such layer, and the like.

A. Definitions

In describing the present invention, the following terms will be employed, and are intended to be defined as indicated below.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of 1 to 6 carbon atoms, preferably 1 to 4 carbon atoms.

The term "alkenyl" as used herein refers to a branched or unbranched hydrocarbon group of 2 to 24 carbon atoms containing at least one carbon-carbon double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like. Preferred alkenyl groups herein contain 2 to 12 carbon atoms and 2 to 3 carbon-carbon double bonds. The term "lower alkenyl" intends an alkenyl group of 2 to 6 carbon atoms, preferably 2 to 4 carbon atoms, containing one —C=C— bond.

The term "alkynyl" as used herein refers to a branched or unbranched hydrocarbon group of 2 to 24 carbon atoms containing at least one —C≡C— bond, such as ethynyl, n-propynyl, isopropynyl, n-butynyl, isobutynyl, t-butynyl, octynyl, decynyl and the like. Preferred alkynyl groups herein contain 2 to 12 carbon atoms. The term "lower alkynyl" intends an alkynyl group of 2 to 6, preferably 2 to 4, carbon atoms, and one —C≡C— bond.

The term "halogen" as used herein refers to fluorine, chlorine, bromine and iodine.

A coated particle depicted, for example, as "$CdS@SiO_2$" is intended to refer to a core particle comprising CdS having a coating comprising $SiO_2$.

The term "bifunctional ligand" is used herein in its broadest sense to refer to any mono- or polydentate ligand comprising a first functional group capable of binding to a particle and a second functional second capable of binding to the coating. Preferably, the first functional group attaches to a particle and the second functional group attaches to a coating via one or more attachment points. Optionally, the bifunctional ligand may comprise a spacer between the first and second functional groups.

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl where there is substitution.

A stabilized particle and method of preparing stabilized particles are provided herein. Stabilization of the particles is achieved by providing a coating on the particle that is insulating, semiconducting, metallic or combinations thereof. The coating is attached to the particle through a bifunctional ligand comprising a first functional group and a second functional group.

The particle is preferably a nanoparticle having a size of less than about 0.1 microns, i.e., 100 nanometers. Preferably the particles have a diameter less than 40 nm. Larger particles may suffer from sedimentation problems during the coating process. The particles may vary in shape from generally spherical, through ellipsoid to cylindrical or rod like. For non spherical particles the effective diameter is $(abc)^{1/3}$ where a, b and c are the coordinate axes of the particles. Accordingly, for rod-like particles where a=b<<c, the length (c) of the rods may exceed 100 nm provided $(abc)^{1/3}$ is less than 100 nm. Preferably $(abc)^{1/3}$ is less than 20 nm to obtain optical transparency. There may be a distribution of particle size and in this specification we refer to diameters as the number average. Relatively narrow size distributions are preferred as a small proportion of large particles may cause undesirable light scattering or sedimentation. The particle can comprise a metal, such as copper, silver, gold, platinum, or the like, or a metal compound or alloy such as a metallic sulphide, a metallic arsenide, a metallic selenide, a metallic telluride, a metallic oxide, a metallic halide or a mixture thereof. Preferred particles are semiconductor nanoparticles. Examples of semiconductor nanoparticles include cadmium sulphide (CdS), germanium (Ge), silicon (Si), silicon carbide (SiC), selenium (Se), cadmium selenide (CdSe), cadmium telluride (CdTe), zinc sulphide (ZnS), zinc selenide (ZnSe), zinc oxide (ZnO) and the like. These semiconductor nanoparticles are known to exhibit strong photoluminescence in the visible range of the electromagnetic spectrum. Some organic polymers, such as poly(pyrrole), also form conducting fluorescent particles and precipitate as nanoparticles. Such polymer nanoparticles can also be stabilized using the method disclosed herein.

The source of the particles may be either the particles per se, a compound containing the particles or two or more compounds which when combined form the particles. For example, $Cd(NO_3)_2$ and $Na_2S$ may be combined to form the semiconductor CdS. In the case of metal cores, the source of the particles is usually a metal salt that can be reduced to form metal particles with desired size and morphology, for example, $AuCl_4^-$ is a source of gold particles and $AgNO_3$ is a source of silver particles. The particles to be coated may already be of a core/shell structure or a coat cored structure. In this case the particles can therefore have multiple coating layers.

The particle is coated with a coating layer. Preferably the coating thickness is between 10 and 30 nm. At coating thicknesses less than 10 nm coated particles may exhibit some colloidal instability. If coating thickness significantly exceeds 30 nm the coated particles may cause undesirable light scattering. Preferably the coated particles are also nanoparticles. The coating is bonded to the particle through a bifunctional ligand. The bifunctional ligand is represented by the formula:

wherein A, B and X are defined as above.

The first functional group, A, is a chemical entity or group that can bind specifically to a particle and therefore alter the surface state and surface trap energies that control or affect surface fluorescence and nonradiative decay pathways in photoexcited nanoparticles. The first functional group can be monodentate or polydentate, which may enhance bonding to the particle. It will be understood that the first functional group chosen will depend on the type of particle being coated. The structure of the first functional group may also change when it is bound to the surface of the particle. For instance, when the first functional group is —$NH_2$, then only N bonds to the particle surface. In the case of —SH, only S bonds to the particle surface. The first functional group can be selected so as to bind to a particle that has been coated according to the method disclosed herein, thereby providing a particle comprising more than one coating layer.

The second functional group is a chemical entity or group which has the ability to activate the surface of the core particle for nucleation of a coating layer. The second functional group may also activate the fluorescence in the coating layer. It will be appreciated that the second functional group chosen will depend on the type of coating to be deposited. For example, silane second functional groups activators are usually negatively charged in water at a pH of greater than two. A cationic second functional group such as $NR_4^+$, wherein R is an alkyl group such as methyl or ethyl may be more efficacious for deposition of anionic coating species such as $AuCl_4^-$, $PtCl_6^{2-}$ or $SnO_3^{2-}$. In some cases, it may be useful to apply an organic coating such as a conducting polymer to the surface to aid electron transfer from the activated core particle. In this case, the second functional group could be an unsaturated ethylene or allyl group which can couple to the alkyl chains of the polymer coating. The activating group will then be optimized for coupling to any functional groups on the backbone or on pendent groups of the polymer coating. A bifunctional ligand comprising such a coating activator will permit activated core particles to be coated with conducting layers that can be embedded into organic films such as plastics.

Suitable spacers include, but are not limited to, straight chain, branched or cyclic hydrocarbons such as alkyl, alkenyl or alkynyl spacers that optionally can be substituted with halide groups such as fluoride, chloride, bromide or iodide. Preferably, the spacer is an alkyl or fluoroalkyl chain.

Specific examples of bifunctional ligands include are 3-mercaptopropyl trimethoxysilane [$SH(CH_2)_3(Si(OMe)_3)$] ("MPS"), 1,3-propanedithiol [$(HS(CH_2)_3SH)_2$], 3-aminopropanethiol [$(HS(CH_2)_3NH_2)$] ("APT") and 3-amino propyl trimethoxysilane [$NH_2(CH_2)_3Si(OMe)_3$] ("APS"). In one preferred embodiment, the bifunctional ligand is MPS, APT or APS. In these ligands, the mercapto or thiol and amino groups function as the first functional group and the trimethoxysilane group functions as the second functional group. In an other preferred embodiment the second functional group may be another alkoxysilane group such as $(Si(OEt)_3$ or any other hydrolysable functional group such as Si $(OPr)_3$. In other words the second functional group can be a hydrolysable functional group having the structural formula $(Si(OR)_3)$, wherein R is an alkyl group, preferably a lower alkyl group. While in this specification the Examples illustrate R being a methyl group other alkyl, especially lower alkyl groups could also be used to provide suitable coatings. The propyl group acts as a spacer. When the activator is $HS(CH_2)_3SH$, the core particle will be activated by the SH groups and its surface will also be coated with those groups which bind strongly to most metal ions including $Cd^{2+}$ and $Ag^+$. This surface is then suitable for nucleation of a metal sulfide coating such as CdS, CdSe or ZnSe or a metal coating per se such as Ag or Au.

It will be appreciated that the coating may be selected from the same material as the core particles. Suitable insulating, semiconducting and/or metallic coatings include silica, Se, organic conducting polymers such as poly (pyrrole), metal oxides such as titania ($TiO_2$), zirconia ($ZrO_2$), alumina ($Al_2O_3$), zinc oxide (ZnO), tin dioxide ($SnO_2$) or manganese oxide (MnO), metal sulphides such as CdS and ZnS, metal selenides such as CdSe and ZnSe, metal tellurides such as CdTe and ZnTe, metal halides such as silver iodide (AgI) and silver bromide (AgBr), catalytically active metals such as platinum, palladium, iridium or alloys and mixtures thereof, metals with unusual optical properties such as bismuth or metals per se such as copper, silver or gold. Silica is a preferred coating due to its ability to dissolve in various solvents and resistance to coagulation. The coating is preferably homogeneous and microporous which protects the particles for example from photochemical degradation. However, it will be understood that the tern "coating" is used herein in its broadest sense and refers to both partial and complete coatings, as well as to multiple layers of coatings. While a complete coating is desirable, it may not be possible as a consequence of experimental limitations or because the required effect is achievable with an incomplete coating.

The source of the coating may be either the coating per se, a compound containing the coating or two or more compounds which when combined form the coating. When the coating is silica, sodium silicate may be an appropriate source. Addition of $Cd^{2+}$ and $H_2Se$ at an optimal rate to activated particles will generate particles coated with CdSe. Alternatively, slow reduction of $AuCl_4^-$ can be used to coat particles with gold onto the mercapto-activated surface described above.

For metal oxide or hydroxide coatings, control of pH can be used to optimize the coating conditions. When coating with silica, deposition occurs optimally at a pH of about 9 to about 12. The silane activator ligand is then negatively charged, which favors the deposition of cationic species. However, very high pH often causes precipitation of metal hydroxide or oxide so quickly that the coating cannot compete. For example, in the case of alumina or titania deposition onto silane-activated core particles, a lower pH may provide slower hydrolysis and less nucleation of pure coating particles at the expense of weakening the attraction between the silane groups and the metal cations in solution. An optimal pH exists which minimizes separate coating particle formation whilst maximizing deposition onto the activated surface. For metal oxide coatings such as $Al_2O_3$, $TiO_2$, $ZrO_2$ and $SnO_2$, silane groups are the simplest and cheapest activator to use, but specially synthesized activators containing, for example, Ti, Al or Sn alkoxide groups as coating activators may be more efficacious.

The surface reactions involved in attaching silica to MPS are illustrated in FIG. 1.

The first two steps of the method disclosed and claimed herein comprise (i) reacting a source of particles with a source of coating and (ii) adding a bifunctional ligand of the formula A—X—B wherein A, X, and B are as defined above. Alternatively, the source of particles may first be reacted with the bifunctional ligand, followed by addition of the coating. These first two steps may be carried out in any suitable solvent, preferably water and/or an alcohol such as ethanol. The particle size may be influenced by the order of addition of the reagents. Each reagent is generally added with stirring using any suitable known technique, for example, magnetic stirring. After the particle, bifunctional reagent and coating are admixed, the bifunctional ligand and coating are allowed to deposit onto the particle. The duration of the deposition step may be from about 6 hours to about 7 days so as to ensure that the coating has deposited onto the modified particle surface.

The coated particles may then be transferred into a suitable solvent such as an alcohol, e.g., ethanol, so that any excess dissolved coating that may be present precipitates out onto the coated particle thereby increasing the thickness of the coating thereon.

In another embodiment, the method described in Stöber et al. (1968) *J. Colloid Interface Sci.* 26:62 can be used for further coating growth when the coating is silica. Briefly, this technique involves the base-catalyzed hydrolysis of tetraethoxysilane ("TES") and subsequent condensation/polymerization of silica monomers onto the existing coated particles.

The stabilization of the particles of the present invention inside a coating preserves their unique properties such as fluorescence. In addition, the coating substantially prevents photochemical degradation of the particles which can be advantageous in high temperature or optical applications. The coating may also enable these particles to be dispersed in a wide variety of matrices including glasses, polymers and solvents.

Coated particles as disclosed and claimed herein find utility as detectable labels for use in a variety of contexts. For example, a method is provided for determining the presence of an analyte in a sample suspected of containing the analyte comprising incubating the sample with a ligand that specifically binds to the analyte and is capable of providing a detectable signal by virtue of the presence of a coated particle as part of the ligand. The ligand can be any molecule that can specifically bind to the analyte. Thus, the ligand can be an antigen- or epitope-specific monoclonal or polyclonal antibody, a poly- or oligonucleotide comprising a nucleic acid sequence complementary to the nucleic acid sequence of a poly- or oligonucleotide analyte, a receptor agonist or antagonist capable of binding specifically to a cellular receptor molecule, e.g., a cell surface receptor molecule, a cytoplasmic receptor molecule, a nuclear receptor molecule, or the like. The coated particle can be attached to the ligand using methods that are well known in the art.

A coated particle-ligand composition is added to the sample and incubated therewith for a period of time sufficient for the coated particle-ligand to bind to the analyte to form a coated particle-ligand:analyte complex. The amount of coated particle-ligand composition and the period of time required for the coated particle-ligand composition to bind to the analyte can be determined using any method routine in the art. The coated particle-ligand:analyte complex can be separated from unbound coated particle-ligand composition using methods such as filtration, centrifugation and the like. The presence of a coated particle-ligand:analyte complex can be detected using fluorescence, photoluminescence, absorption, diffraction or scattering methods. The amount of coated particle-ligand:analyte complex detected can be quantitated by comparison with a standard curve prepared using samples containing known concentration of the analyte.

Possible additional applications for these stabilized particles may be in the fields of pigments, paints, fabrics, optics such as fluorescence and electronics.

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

General Experimental

Tetraethoxysilane ("TES"), sodium silicate ($Na_2O(SiO_2)_{3-5}$ (27 wt. % $SiO_2$) were purchased from Aldrich. $Cd(NO_3)_2$ (Merck), $Na_2S$ (Sigma) and 3-mercaptopropyl trimethoxysilane (MPS) were used. Technical grade ethanol (Panreac) and distilled water were used in all the preparations.

Transmission electron microscopy ("TEM") was carried out using a Philips CM20 microscope operating at 200 kV. Samples were prepared by allowing a drop thereof to evaporate on top of a carbon-coated copper grid. UV-visible spectra were measured with a HP 8453 diode array spectrophotometer in 1-cm path length quartz cuvettes.

EXAMPLE 1

Preparation and Characterization of a CDS Particle Coated with Silica

The general procedure for the preparation of $CdS@SiO_2$ colloids comprised the following steps.

To 45 mL of distilled water, 2.0 mL of $Cd(NO_3)_2$ $10^{-2}$ M, 2.5 mL $Na_2$ S $8\times10^{-3}$ M and 0.25 mL of 1 wt. % sodium citrate solution were added under vigorous stirring and a nitrogen atmosphere. The final CdS particle concentration was 0.4 mM.

To 50 mL of the CdS solution was added 0.5 mL of a freshly prepared aqueous solution of MPS (1 mM) under vigorous magnetic stirring. Sodium silicate (2.0 mL of a 0.54 wt. % solution, pH 10.5) was added, again under vigorous stirring. The resulting dispersion (pH>8.5), particle size 5–10 nm, was allowed to stand for 5 days, so that silica slowly polymerized or formed onto the modified CdS particle surface. The dispersion of silica-coated CdS particles was transferred into ethanol, so that the excess dissolved silicate precipitated out (mainly on the existing cores), increasing the shell thickness.

The method described in Stober et al., supra, was then used for further growth. This method comprised the base-catalyzed hydrolysis of TES and subsequent condensation/polymerization of silica monomers onto the existing nuclei.

A. Stabilization with Citrate

Citrate ions have been used as protective agents for a variety of inorganic colloids. Different citrate/$Cd^{2+}$ concentration ratios were tested, finding an optimal value of 0.45, which was used for all the remaining experiments. The average particle size of the CdS particles obtained through this process was 7 nm.

CdS can be degraded under the influence of light in the presence of dissolved oxygen. The action of oxygen consists of an oxidation of sulphide radicals arising through the formation of hole-anion pairs at the particle surface:

$$S_s^- + O_2 \rightarrow S_s + O_2^- \quad (I)$$

wherein subscript s indicates a surface atom.

This process can be inhibited through the addition of excess sulphide ions, although an alternative and cleaner way is to carry out the reaction under nitrogen atmosphere. When the synthesis is performed in the absence of oxygen, i.e., under a nitrogen atmosphere, the colloid prepared is stable against photodegradation for weeks, allowing for modifications to be performed on it without further precautions.

B. The Role of MPS

The adhesion of silicate moieties at the particle surface can only be made effective when a silane coupling agent is present in the solution. Such a coupling agent acts as a surface primer for making the colloid surface vitreophilic and facilitating silicate deposition.

In the case of a particle of CdS, MPS was chosen since it contains a mercapto group that can bond directly to surface Cd sites, leaving the silane groups pointing toward solution, from where the silicate ions approach the particle surface. These silicate ions build up a first silica shell which permits the transfer into ethanol without particle coagulation. It was observed that the presence of a very thin silica shell is not sufficient to prevent photodegradation, which is mainly attributed to the presence of pores which are large enough to permit the diffusion of $O_2$ molecules through them.

C. Transfer into Ethanol

The solvent exchange process plays two important roles: on the one hand it serves to precipitate out all the silicate moieties (monomers or oligomers) still present in the solution due to a sudden decrease in solubility and on the other hand, it is necessary for the growth of thicker shells when desired. An appropriate ethanol:water volume ratio (at which maximum silicate deposition on the cores is achieved whilst spontaneous nucleation of silica particles is minimised) was found to be between about 4:1 and about 5:1.

D. Transmission Electron Microscopy

Figures 3A, 3B:
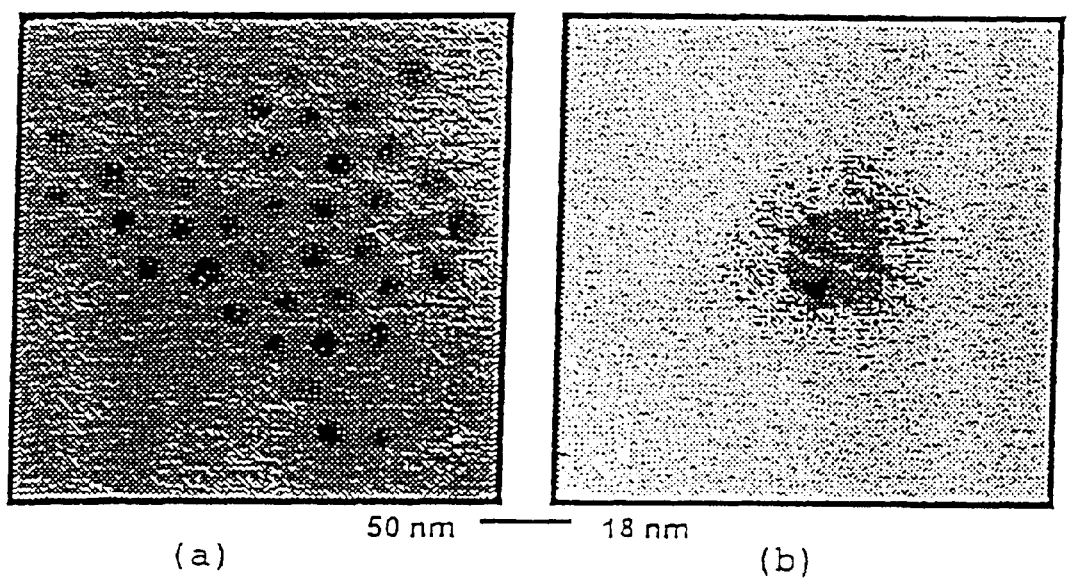
FIG. 3A is an electron micrographs of silicate-stabilized CdS particles prepared in water.
FIG. 3B is an electron micrograph of silicate stabilized $CdS@SiO_2$ particles prepared by transfer into ethanol, producing a sudden silica deposition. The scaling of the micrographs is as indicated.
Figure 4B:
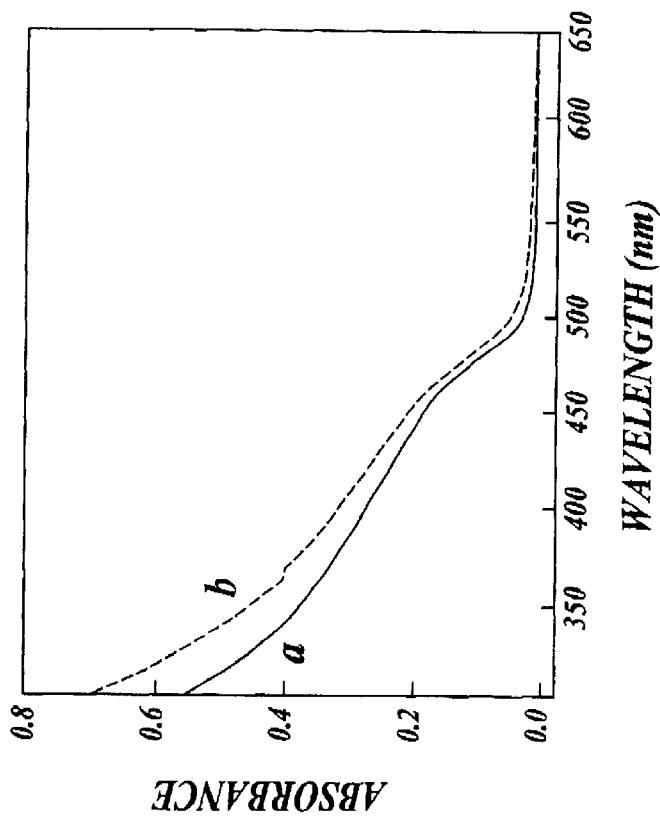
FIG. 4A and FIG. 4B depict UV-visible spectra illustrating photocorrosion of CdS nanoparticles and $Cd@SiO_2$ nanoparticles, respectively, after 0 hours (solid line), 24 hours (dashed line) or 48 hours (dotted line) of exposure to UV light.
Figure 4A:
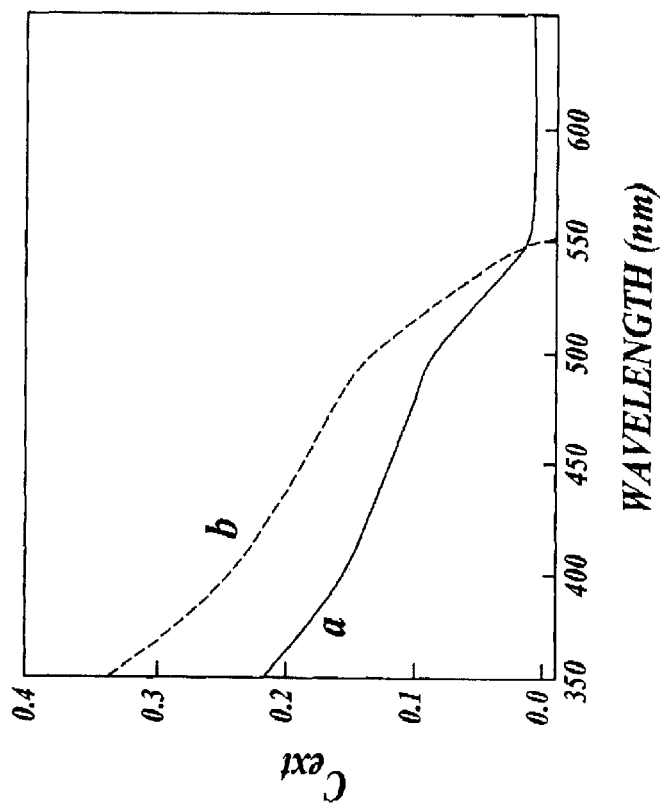

FIG. 3 shows the appearance under the TEM of the particles prepared following the method described. The slightly higher electron absorption by CdS than by $SiO_2$ provides a sufficient contrast to show the core homogeneously surrounded by the silica shell. As shown in FIG. 3, the crystalline nature of the CdS particles can be observed, in contrast with the amorphous silica shell. Both core-free and multiple-core silica particles are formed as well during the transfer into ethanol. The shell can be made thicker and the particle surface smoother by the addition of ammonia and TES, resulting in monodisperse silica spheres with CdS cores placed at their centers.

E. Stabilization Against Photodegradation

Figure 5A:
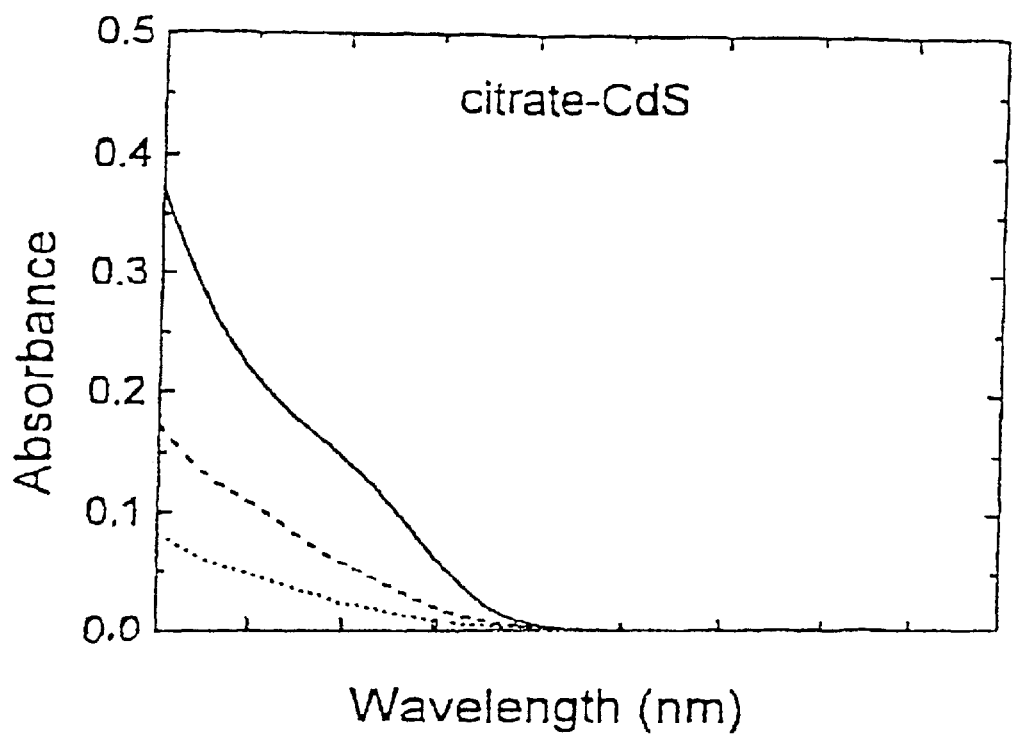
FIG. 5A depicts UV-visible spectra of $CdS@SiO_2$ nanoparticles calculated using Mie theory wherein the dashed and solid lines represent the spectrum for nanoparticles prepared in water and after transfer into ethanol, respectively.
Figure 5B:
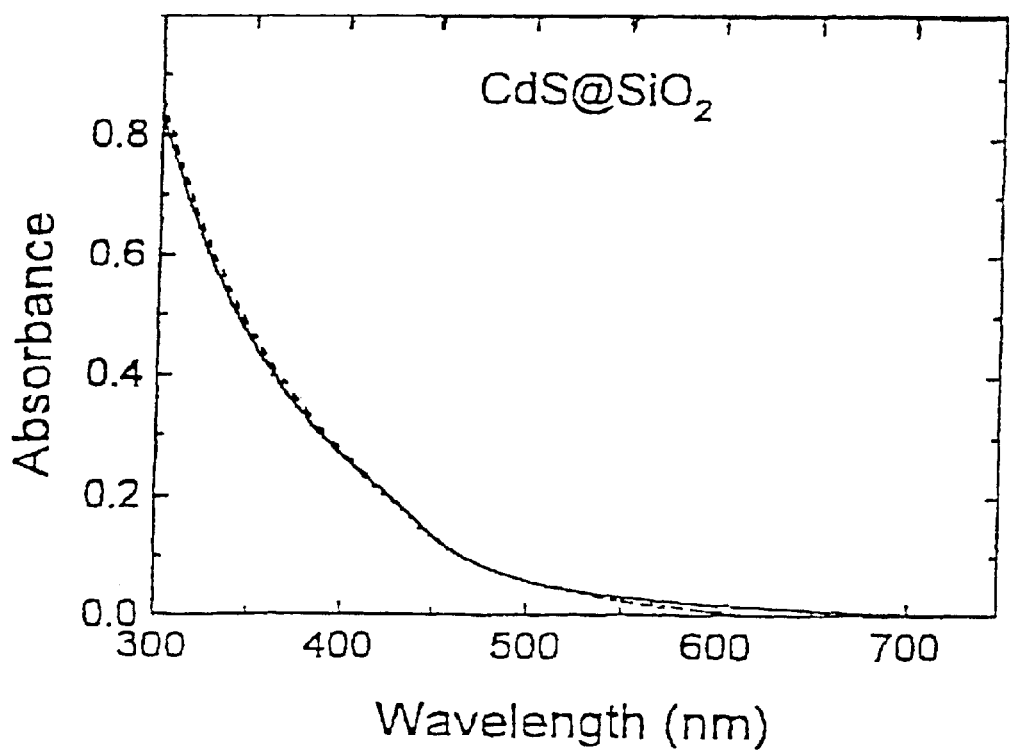
FIG. 5B depicts experimentally determined UV-visible spectra of $CdS@SiO_2$ particles prepared in water (solid line) and after transfer into ethanol (dashed line).

Silica-coated particles are far more stable against photodegradation than uncoated particles, so that samples could be stored in light for several weeks with negligible variation of their absorption spectra. As an example, FIG. 5 shows the time evolution of the spectra of the citrate-stabilized particles, as compared with silica-coated ones. This effect can be related to the small pore size of the silica shells grown in ethanol through monomer addition which makes it very difficult for $O_2$ molecules to reach the particle surface. Such a protection would be of great importance in the preparation of stable nanostructured materials with practical applications.

F. Optical Properties of Silica-Coated CdS

The optical properties of dispersions of spherical particles can be predicted by Mie theory (M. Kerker, The Scattering of Light and Other Electromagnetic Radiation (Academic Press, New York, 1969)). According to this theory, the extinction coefficient of the dispersion at a given wavelength depends on the complex dielectric constant of the particles at that wavelength and on the refractive index of the solvent. Particle size is a parameter with special significance for metal and semiconductor particles, which show quantum size effects.

Figure 2:
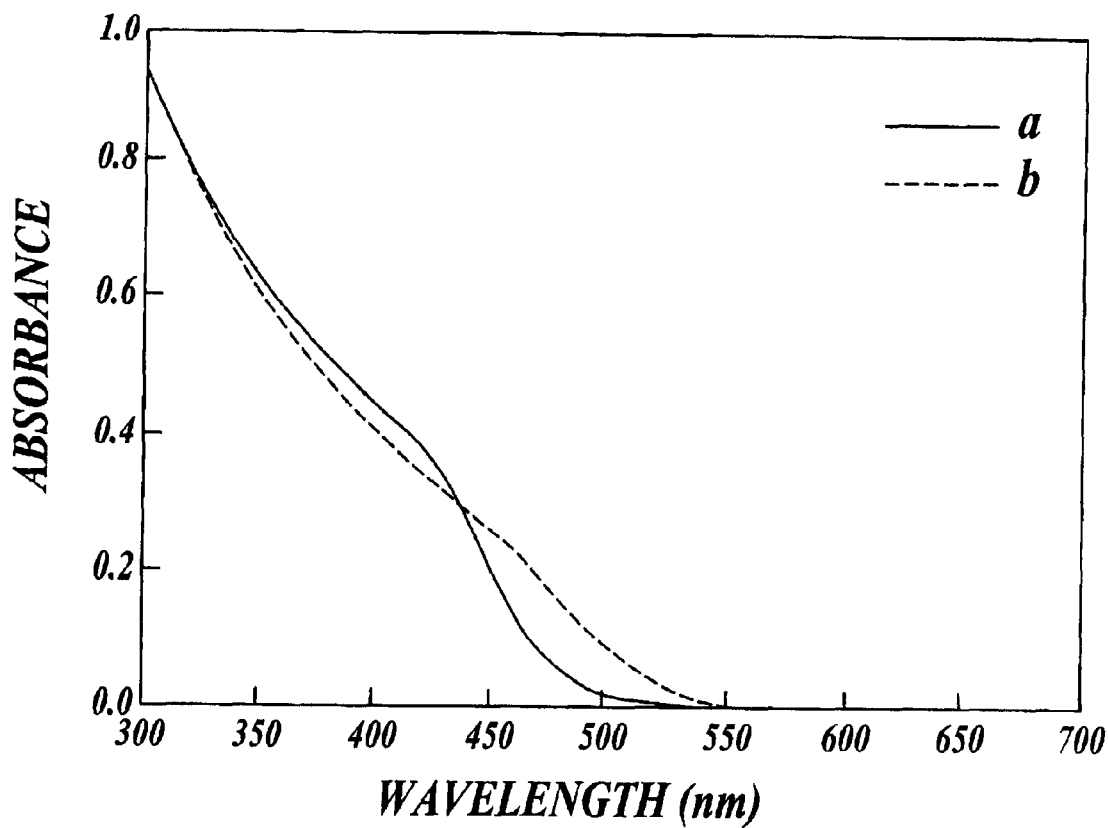
FIG. 2 depicts UV-visible spectra of CdS nanoparticles prepared in water using sodium silicate as a stabilizer wherein the solid line represents addition previous to nanoparticle formation and the dashed line represents addition after nanoparticle formation.

When Mie theory is adapted to core-shell particles, the dielectric data for both the core and the shell materials need to be taken into account. For silica, only the real component of the dielectric constant was considered, using the square of the refractive index (1.456). The spectra for bare CdS spherical particles were calculated with a diameter of 6 nm and of the same particles surrounded by a 5 nm thick silica shell. These spectra are compared in FIG. 5 with the experimental spectra of samples obtained by transfer into ethanol of small CdS particles and subsequent growth with TES. The agreement between both plots is fairly good, showing for the silica-coated particles an increased extinction mainly at wavelengths lower than the absorption onset and showing that the optical properties of the CdS particles are neither significantly altered by Silica deposition, nor that the silica deposition when carried out as described herein leads to significant coalescence or aggregation. This is also confirmed by the results set out in FIG. 2.

G. Electroluminescence

Figure 6:
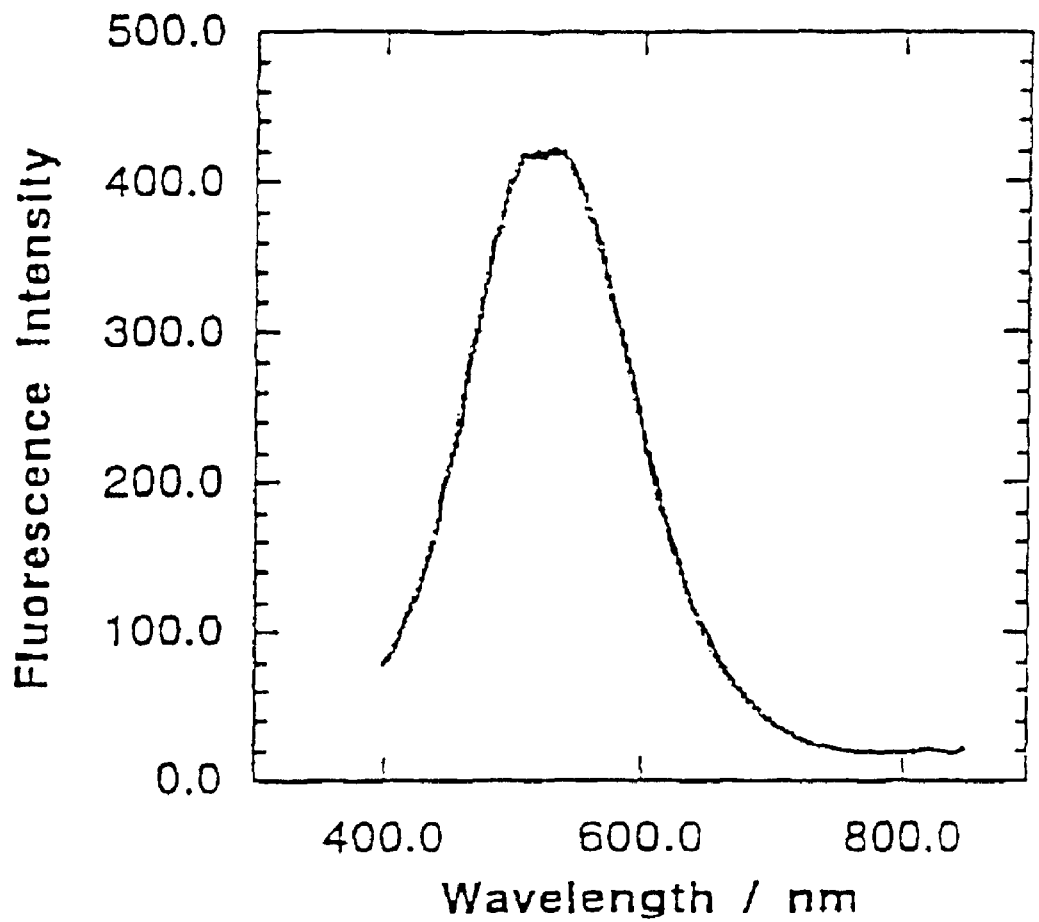
FIG. 6 depicts a photoluminescence spectrum of $CdS@SiO_2$ prepared using 3-mercaptopropyl trimethoxysilane as a bifunctional ligand.

In FIG. 6, the photoluminescence spectrum of CdS@SiO$_2$ particles is shown. The excitation wavelength is 400 nm. A strong, broad peak with a maximum intensity at 580 nm was observed. This is attributed to the recombination of trapped charge carriers in surface states at the CdS-silica interface. The density of surface states has been dramatically enhanced by the adsorption of MPS, yielding strong fluorescence readily visible to the human eye. These coated particles can be concentrated by rotary evaporation to form more viscous solution or, if required, can be made more viscous by addition of polymers such as poly(vinyl) alcohol, poly (vinyl) acetate or poly(acrylic) acid. However, this affects only the deposition conditions and is not critical.

A colloid film is prepared by applying such a viscous polymeric preparation to indium tin oxide (ITO) glass (1 cm×1 cm) on a spin coater (1000 rpm) via a micropipette.

Other coating methods such as dip coating, screen printing or spray coating may also be used. The film can be made thicker by drying the coated particles in an oven at <100° C. and then reapplying second or multiple coatings. Optimal volumes and spin speeds depend on the exact viscosity of the colloid solution applied.

Figure 7:
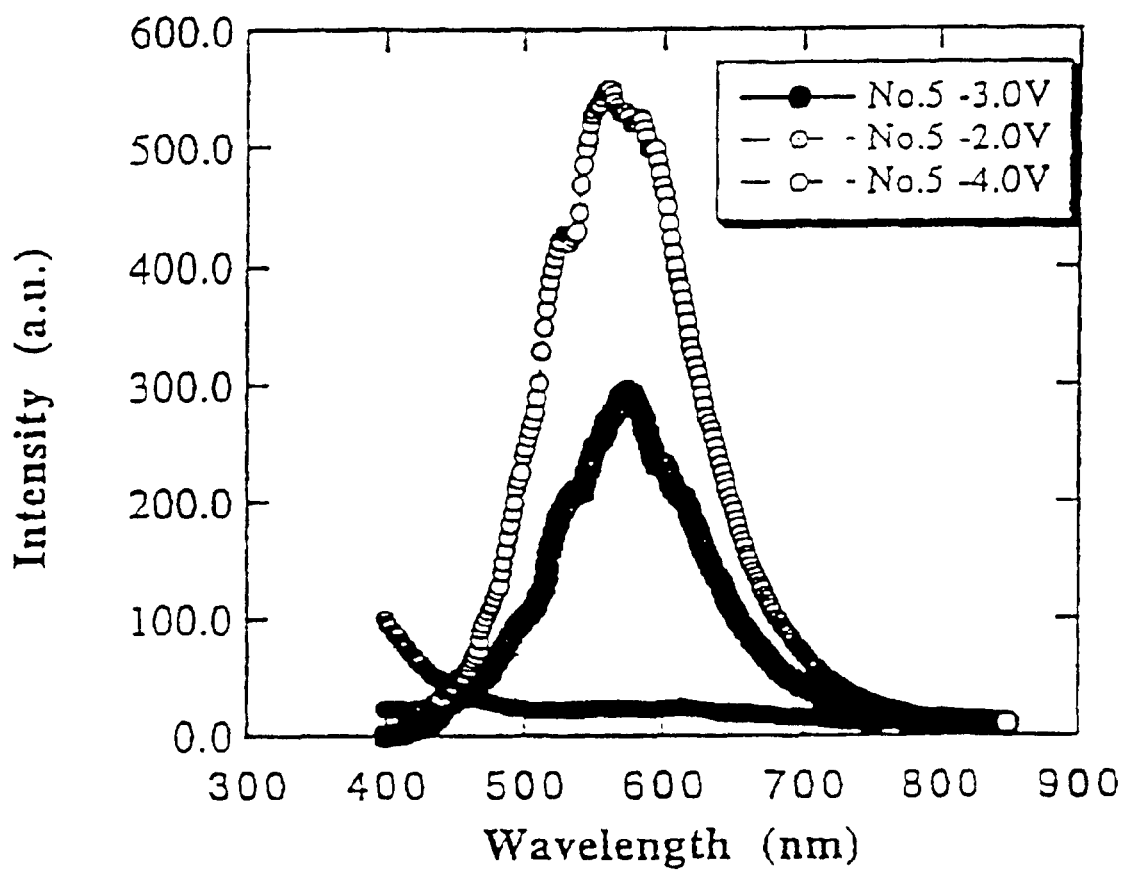
FIG. 7 depicts electroluminescence spectra observed from $CdS@SiO_2$ particles prepared using 3-mercaptopropyl trimethoxysilane as bifunctional ligand.

Electroluminescence was demonstrated by polarizing the ITO electrode coated with a thin film of CdS@SiO$_2$ particles in a solution of potassium persulfate (1 M) at pH 13. The solution also contained a Ag/AgCl reference electrode and a platinum flag counter electrode. As the potential of the ITO electrode is made more negative, light is observed from the electrode as shown in FIG. 7. The intensity increases as the potential is made more negative. The intensity depends in a complicated way on applied voltage, electrode resistance and solution composition. Electroluminesence spectra at three potentials are shown. These spectra indicate that the coating, while protecting the particles from coalescence, still allows charge transfer and electroluminescence processes to proceed at the surface of the particles. The silica coating allows the particle size and fluorescence properties of the particle film to be tailored to yield optimal colour and efficiency and then coated without affecting the particle characteristics. By maintaining the small sizes, light scattering from the particle film and the associated intensity losses are also minimized.

EXAMPLE 2

Preparation and Characterization of a SE Particle Coated with Silica

A coated semiconductor nanoparticle was prepared according to the method described in Example 1, with the exception that selenium (Se) was substituted for CdS. The Se@SiO$_2$ nanoparticles had properties similar to those determined for CdS@SiO$_2$ particles.

EXAMPLE 3

Preparation and Characterization of a SI Particle Coated with Silica

A coated semiconductor nanoparticle was prepared according to the method described in Example 1, with the exception that silicon (Si) was substituted for CdS. The Si@SiO$_2$ nanoparticles were expected to have properties similar to those determined for CdS@SiO$_2$ particles.

EXAMPLE 4

Preparation and Characterization of a CD SE Particle Coated with Silica

A coated semiconductor nanoparticle was prepared according to the method described in Example 1, with the exception that cadmium selenide (CdSe) was substituted for CdS. The CdSe@SiO$_2$ nanoparticles had properties similar to those determined for CdS@SiO$_2$ particles.

EXAMPLE 5

Preparation and Characterization of a CD TE Particle Coated with Silica

A coated semiconductor nanoparticle was prepared according to the method described in Example 1, with the exception that cadmium telluride (CdTe) was substituted for CdS. The CdTe@SiO$_2$ nanoparticles had properties similar to those determined for CdS@SiO$_2$ particles.

EXAMPLE 6

Preparation and Characterization of a ZNS Particle Coated with Silica

A coated semiconductor nanoparticle was prepared according to the method described in Example 1, with the exception that zinc sulfide (ZnS) was substituted for CdS. The ZnS@SiO$_2$ nanoparticles had properties similar to those determined for CdS@SiO$_2$ particles.

EXAMPLE 7

Preparation and Characterization of a ZNSE Particle Coated with Silica

A coated semiconductor nanoparticle was prepared according to the method described in Example 1, with the exception that zinc selenide (ZnSe) was substituted for CdS. The ZnSe@SiO$_2$ nanoparticles had properties similar to those determined for CdS@SiO$_2$ particles.

EXAMPLE 8

Preparation and Characterization of a ZNO Particle Coated with Silica

A coated semiconductor nanoparticle was prepared according to the method described in Example 1, with the exception that zinc oxide (ZnO) was substituted for CdS. The ZnO@SiO$_2$ nanoparticles had properties similar to those determined for CdS@SiO$_2$ particles.

EXAMPLE 9

Preparation and Characterization of an AgI Particle with Silica

A 100 mL solution containing KI ($8 \times 10^{-4}$ M) and sodium citrate (1 mM) was prepared and stirred rapidly using a magnetic stirrer. A solution of 5 mL 0.01M of AgNO$_3$ was added by pipette. The solution immediately turned from clear to transparent yellow, indicating the formation of small AgI crystallines. Within 5 minutes, APS (1 mM, 0.5 mL) is added. After 20 minutes, active silicate ion was added, prepared as outlined before. A thin shell of silica was deposited after 24 hours.

EXAMPLE 10

Preparation and Characterization of an Au Particle Coated with Silica

Au particles from 40–80 nm in diameter were grown from seed particles prepared via the Turkevich method. (Enüstün B. V.; Turkevich, J J. Am.Chem.Soc. 1963 85 3317).
Seed Gold Sol
100 mL of 0.5 mM HAuCl$_4$ was heated with mild stirring until boiling. A boiling solution of 5 mL 0.5 mM tri-sodium citrate was added to the HAuCl$_4$ solution with rapid stirring. The resulting solution was then boiled for approximately 15 minutes with stirring. Finally, the solution was allowed to cool.
Large Particles
A 50 mL solution containing 25 nM 15 nm Au colloid and 1.5 mL NH$_2$OH.HCl was prepared. 3 drops 1M KOH was added to 70 mL of 1 mN HAuCl$_4$, raising the pH from approximately 3 to 4. 50 mL of HAuCl$_4$ solution was added dropwise (at a rate of approximately one drop every two seconds) to the Au colloid solution with stirring.

The new particle volume was calculated from the initial and final gold ion concentrations and the initial particle size. Such particles are large, reasonably spherical though they contain angular and rod like particles. They are purple in transmitted light but scatter yellow light strongly. They settle out of solution over hours if left standing. The surfaces have both adsorbed citrate and adsorbed hydroxylamine, which are displaced by APS. Coating is effected by the procedure of Example 1.

EXAMPLE 11

Preparation of an Au Particle with a $SnO_2$ Coating

The APS also enhances deposition of other oxide coatings. Particularly important are conducting or semiconducting layers, which allow electron transport between the core and exterior.

10 mL of 0.045M $Na_2SnO_3.3H_2O$ was acidified to pH 10.5 by addition of 3 drops 1M nitric acid. 25 μL of 1 mM APS was added to 5 mL of 0.5 mM 15 nm Au colloid dropwise with stirring. 15 minutes later, 1 mL of the stannate solution was added to the Au colloid solution with stirring. A colour change became apparent in the solution after one week.

The colour of the ruby red gold sol turned a purple-crimson as coating took place. The coating obtained this way was about 5–10 nm thick, and was dependent on the ageing time, the pH of ageing and the stannate ion concentration. It also depended on the gold colloid concentration and the stirring rate.

Accordingly, stabilized nanoparticles and methods for preparing stabilized nanoparticle have been disclosed. Although preferred embodiments of the subject invention have been described in some detail, it is understood that obvious variations can be made without departing from the spirit and the scope of the invention as defined by the appended claims.

What is claimed is:

1. A method for preparing a coated particle, comprising:
   (i) admixing a source of the particle with a source of coating to provide a particle-coating admixture;
   (ii) adding to the particle-coating admixture a bifunctional ligand having structural formula (I):

   A—X—B wherein A is a first functional group that attaches to the particle, or to a coating formed on the particle, B is a second functional group that activates the surface of the core particle for nucleation of a coating layer and X is an optional linking group; and
   (iii) allowing the bifunctional ligand and coating to deposit on the particle.

2. A method for preparing a coated particle, comprising:
   (i) admixing a source of the particle with a bifunctional ligand having structural formula (I):

   A—X—B wherein A is a first functional group that attaches to the particle, or to a coating formed on the particle, B is a second functional group that activates the surface of the core particle for nucleation of a coating layer and X is an optional linking group, to provide a particle-ligand admixture;
   (ii) adding to particle-ligand admixture a source of coating; and
   (iii) allowing the bifunctional ligand and coating to deposit on the particle.

3. The method of claim 1 or claim 2, wherein the particle is a nanoparticle.

4. The method of claim 3, wherein the nanoparticle comprises a metal or a metal compound.

5. The method of claim 4, wherein the nanoparticle comprises a metal selected from the group consisting of copper, silver, gold and platinum.

6. The method of claim 4, wherein the nanoparticle comprises a metal compound selected from the group consisting of a metallic sulfide, a metallic arsenide, a metallic selenide, a metallic telluride, a metallic oxide, a metallic halide and a mixture thereof.

7. The method of claim 3, wherein the nanoparticle is a semiconductor nanoparticle.

8. The method of claim 7, wherein the semiconductor nanoparticle comprises cadmium sulfide (CdS), germanium (Ge), silicon (Si), silicon carbide (SiC), selenium (Se), cadmium selenide (CdSe), cadmium telluride (CdTe), zinc sulfide (ZnS), zinc selenide (ZnSe) or zinc oxide (ZnO).

9. The method of claim 1 or claim 2, wherein A is selected from the group consisting of a thiol, an amine, a phosphine, a phosphate, a borate, a tetra alkyl ammonium, a carboxyl, a silicate, a siloxyl, a selenate, an arsenate and an aluminate.

10. The method of claim 1 or claim 2, wherein B is selected from the group consisting of a thiol, an amine, a phosphine, a carboxyl, a silicate, a siloxyl, a silane, a selenate, an arsenate and an aluminate.

11. The method of claim 1 or claim 2, wherein X is present and is a straight chain, branched or cyclic hydrocarbon selected from the group consisting of alkyl, alkenyl and alkynyl, optionally substituted with a fluoride, chloride, bromide or iodide.

12. The method of claim 1 or claim 2, wherein the bifunctional ligand is selected from the group consisting of 3-mercaptopropyl trimethoxysilane [$SH(CH_2)_3(Si(OMe)_3)$] (MPS), 1,3-propanedithiol [$(HS(CH_2)_3SH)$] 3-aminopropanethiol [$(HS(CH_2)_3NH_2)$] (APT) and 3-aminopropyl trimethoxysilane [$NH_2(CH_2)_3Si(OMe)_3$] (APS).

13. The method of claim 1 or claim 2, wherein the source of coating is selected from the group consisting of silica ($SiO_2$), Se, an organic conducting polymer, a metal, a metal oxide, a metal sulphide, a metal selenide, a metal telluride, and a metal halide.

14. The method of claim 13, wherein the source of coating is silica.

15. The method of claim 13, wherein the source of coating is a metal oxide selected from the group consisting of titania ($TiO_2$), zirconia ($ZrO_2$), alumina ($Al_2O_3$), zinc oxide (ZnO), tin dioxide ($SnO_2$) or manganese oxide (MnO).

16. The method of claim 13, wherein the source of coating is a metal sulfide selected from the group consisting of CdS and ZnS.

17. The method of claim 13, wherein the source of coating is a metal selenide selected from the group consisting of CdSe and ZnSe.

18. The method of claim 13, wherein the source of coating is a metal telluride selected from the group consisting of CdTe and ZnTe.

19. The method of claim 13, wherein the source of coating is a metal halide selected from the group consisting of silver iodide (AgI) and silver bromide (AgBr).

20. The method of claim 13, wherein the source of coating is a metal selected from the group consisting of platinum, palladium, iridium, bismuth, copper, silver, gold, and alloys and mixtures thereof.

21. A coated particle prepared according to any one of claims 1 to 20.

22. A particle stabilized by a coating, wherein said coating is attached to said particle via a bifunctional ligand having structural formula (I):

A—X—B wherein A is a first functional group that attaches to the particle, or to a coating formed on the particle, B is a second functional group that activates the surface of the core particle for nucleation of a coating layer and X is an optional linking group.

23. The particle of claim 22, wherein the particle is a nanoparticle.

24. The particle of claim 23, wherein the nanoparticle comprises a metal or a metal compound.

25. The particle of claim 24, wherein the nanoparticle comprises a metal selected from the group consisting of copper, silver, gold and platinum.

26. The particle of claim 24, wherein the nanoparticle comprises a metal compound selected from the group consisting of a metallic sulfide, a metallic arsenide, a metallic selenide, a metallic telluride, a metallic oxide, a metallic halide and a mixture thereof.

27. The particle of claim 23, wherein the nanoparticle is a semiconductor nanoparticle.

28. The particle of claim 27, wherein the semiconductor nanoparticle comprises cadmium sulfide (CdS), germanium (Ge), silicon (Si), silicon carbide (SiC), selenium (Se), cadmium selenide (CdSe), cadmium telluride (CdTe), zinc sulfide (ZnS), zinc selenide (ZnSe) or zinc oxide (ZnO).

29. The particle of claim 22, wherein A is selected from the group consisting of a thiol, an amine, a phosphine, a phosphate, a borate, a tetra alkyl ammonium, a carboxyl, a silicate, a siloxyl, a selenate, an arsenate and an aluminate.

30. The particle of claim 22, wherein B is selected from the group consisting of a thiol, an amine, a phosphine, a carboxyl, a silicate, a siloxyl, a silane, a selenate, an arsenate and an aluminate.

31. The particle of claim 22, wherein X is present and is a straight chain, branched or cyclic hydrocarbon selected from the group consisting of alkyl, alkenyl and alkynyl, optionally substituted with a fluoride, chloride, bromide or iodide.

32. The particle of claim 22, wherein the bifunctional ligand is selected from the group consisting of 3-mercaptopropyl trimethoxysilane [SH(CH$_2$)$_3$(Si(OMe)$_3$)] (MPS), 1,3-propanedithiol [(HS(CH$_2$)$_3$SH)] 3-aminopropanethiol [(HS(CH$_2$)$_3$NH$_2$)] (APT) and 3-aminopropyl trimethoxysilane [NH$_2$(CH$_2$)$_3$Si(OMe)$_3$] (APS).

33. The particle of claim 22, wherein the coating is selected from the group consisting of silica (SiO$_2$), Se, an organic conducting polymer, a metal, a metal oxide, a metal sulfide, a metal selenide, a metal telluride, and a metal halide.

34. The particle claim 22, wherein the coating is silica.

35. The particle of claim 33, wherein the coating is a metal oxide selected from the group consisting of titania (TiO$_2$), zirconia (ZrO$_2$), alumina Al$_2$O$_3$), zinc oxide (ZnO), tin dioxide (SnO$_2$) or manganese oxide (MnO).

36. The particle of claim 33, wherein the coating is a metal sulfide selected from the group consisting of CdS and ZnS.

37. The particle of claim 33, wherein the coating is a metal selenide selected from the group consisting of CdSe and ZnSe.

38. The particle of claim 33, wherein the coating is a metal telluride selected from the group consisting of CdTe and ZnTe.

39. The particle of claim 33, wherein the source of coating is a metal halide selected from the group consisting of silver iodide (AgI) and silver bromide (AgBr).

40. The particle of claim 33, wherein the source of coating is a metal selected from the group consisting of platinum, palladium, iridium, bismuth, copper, silver, gold, and alloys and mixtures thereof.

41. A method for determining the presence of an analyte in a sample suspected of containing the analyte comprising:
    (a) providing a coated particle-ligand composition, wherein the ligand is bound to the coated particle and further wherein the coated particle-ligand composition is capable of specifically binding to the analyte and capable of providing a detectable signal;
    (b) incubating the sample with the coated particle-ligand composition to form a coated particle-ligand:analyte complex; and
    (c) detecting the presence of the coated particle-ligand:analyte complex as indicating of the presence of the analyte in the sample and wherein the coated particle comprises a coating attached to said particle via a bifunctional ligand having structural formula (I):

A—X—B wherein A is a first functional group that attaches to the particle, or to a coating formed on the particle, B is a second functional group that activates the surface of the core particle for nucleation of a coating layer and X is an optional linking group.

42. The method of claim 41, wherein the particle is a nanoparticle.

43. The method of claim 42, wherein the nanoparticle is a semiconductor nanoparticle.

44. The method of claim 43, wherein the semiconductor nanoparticle comprises cadmium sulfide (CdS), germanium (Ge), silicon (Si), silicon carbide (SiC), selenium (Se), cadmium selenide (CdSe), cadmium telluride (CdTe), zinc sulfide (ZnS), zinc selenide (ZnSe) or zinc oxide (ZnO).

45. The method of claim 44, wherein the bifunctional ligand is selected from the group consisting of 3-mercaptopropyl trimethoxysilane [SH(CH$_2$)$_3$(Si(OMe)$_3$)] (MPS), 1,3-propanedithiol [(HS(CH$_2$)$_3$SH)] 3-aminopropanethiol [(HS(CH$_2$)$_3$NH$_2$)] (APT) and 3-aminopropyl trimethoxysilane [NH$_2$(CH$_2$)$_3$Si(OMe)$_3$] (APS).

46. The method of claim 45, wherein the coating is selected from the group consisting of silica (SiO$_2$), Se, an organic conducting polymer, a metal, a metal oxide, a metal sulfide, a metal selenide, a metal telluride, and a metal halide.

47. The method of claim 46, wherein the coating is silica.

48. The method of claim 3 wherein the particle is less than 60 nm and preferably less than 40 nm.

49. The method of claim 3 wherein the coating has a thickness of less than 30 nm.

50. The particle of claim 23 wherein the particle size is less than 60 nm and preferably less than 40 nm.

51. The particle of claim 23 wherein the coating has a thickness of less than 30 nm.

52. The method of claim 41 wherein the particles size is less than 60 nm and preferably less than 40 nm.

53. The method of claim 41 wherein the coating has a thickness of less than 30 nm.

* * * * *

UNITED STATES PATENT AND TRADEMARK OFFICE
CERTIFICATE OF CORRECTION

PATENT NO. : 6,548,168 B1
DATED : April 15, 2003
INVENTOR(S) : P.C. Mulvaney et al.

Page 1 of 1

It is certified that error appears in the above-identified patent and that said Letters Patent is hereby corrected as shown below:

Title page,
Item [56], References Cited, FOREIGN PATENT DOCUMENTS, delete as duplicative the following:
"WO    90/15666    12/1990";
"WO    91/09678    7/1991; and
"WO    93/15117    8/1993"
OTHER PUBLICATIONS, after "97-039417/04," insert -- Class A85 G02 L03 (A14 A 26), --; after "28559B/15," insert -- Class L03 R45, JP 54028785 A, --; and after "91-343599/47," insert -- Class L03, JP 03-229635 A, --
Item [57], ABSTRACT,
Lines 5-6, "to said particles via a bifunctional ligand are provided," should read -- to said particles via a bifunctional ligand, are provided, --
Line 6, "as is a method is provided" should read -- as is a method provided --

Column 13,
Line 66, "adding to particle-ligand" should read -- adding to the particle-ligand --

Column 15,
Line 58, "alumina $Al_2O_3$)," should read -- alumina ($Al_2O_3$), --

Column 16,
Line 20, "as indicating" should read -- as indicative --
Line 62, "particles size" should read -- particle size --

Signed and Sealed this

Eighth Day of March, 2005

JON W. DUDAS
*Director of the United States Patent and Trademark Office*